United States Patent
Grilli et al.

(10) Patent No.: US 11,433,043 B2
(45) Date of Patent: Sep. 6, 2022

(54) COMPOUNDS USEFUL FOR INCREASING NEUROGENESIS IN NEURAL TISSUE

(71) Applicant: ALFASIGMA S.P.A., Bologna (IT)

(72) Inventors: Mariagrazia Grilli, Novara (IT); Pier Luigi Canonico, Novara (IT); Aleardo Koverech, Rome (IT)

(73) Assignee: ALFASIGMA S.P.A., Bologna (IT)

( * ) Notice: Subject to any disclaimer, the term of this patent is extended or adjusted under 35 U.S.C. 154(b) by 172 days.

(21) Appl. No.: 16/906,814

(22) Filed: Jun. 19, 2020

(65) Prior Publication Data
US 2020/0323809 A1 Oct. 15, 2020

Related U.S. Application Data (63) Continuation of application No. 15/159,321, filed on May 19, 2016, now abandoned, which is a (Continued)

(30) Foreign Application Priority Data

Jun. 16, 2010 (EP) .................................. 10166094

(51) Int. Cl.
*A61K 31/225* (2006.01)
*A61K 31/21* (2006.01)
(Continued)

(52) U.S. Cl.
CPC .......... *A61K 31/225* (2013.01); *A61K 31/205* (2013.01); *A61K 31/21* (2013.01); *A61P 9/10* (2018.01); *A61P 21/02* (2018.01); *A61P 25/00* (2018.01); *A61P 25/14* (2018.01); *A61P 25/16* (2018.01); *A61P 25/28* (2018.01)

(58) Field of Classification Search
CPC .... A61K 31/205; A61K 31/21; A61K 31/225; A61P 21/02; A61P 25/00; A61P 25/14; A61P 25/16; A61P 25/28; A61P 9/10
See application file for complete search history.

(56) References Cited

U.S. PATENT DOCUMENTS

| 4,194,006 A | 3/1980 | Cavazza |
| 4,254,053 A | 3/1981 | deWitt et al. |

(Continued)

FOREIGN PATENT DOCUMENTS

| EP | 0256999 A2 | 2/1988 |
| EP | 0498144 A1 | 8/1992 |

(Continued)

OTHER PUBLICATIONS

Abdipranolo et al., "The role of neurogenesis in neurodegenerative diseases and its implications for therapeutic development,"CNS & Neurological Disorders—Drug Targets, 7:187-210, 2008.
(Continued)

*Primary Examiner* — Savitha M Rao
(74) *Attorney, Agent, or Firm* — Silvia Salvadori, P.C.; Silvia Salvadori (57) ABSTRACT

The invention described herein is directed to the use of acetyl L-carnitine, or propionyl L-carnitine, or a salt thereof, for preparing a medicament for increasing neurogenesis in neural tissue; in which said increased neurogenesis is useful for preventing central nervous system disorders due to ageing or genetic predisposition.

4 Claims, 7 Drawing Sheets

% MAP2-positive cells (new neurons)

ALC= acetyl L-carnitine; VPA= valproic acid.
Mean ± SD (n=3 exp, in triplicates).
Student's- test; * p<0.05;  p<0.01; * p<0.001; vs vehicle.

Related U.S. Application Data continuation of application No. 13/699,930, filed as application No. PCT/EP2011/059665 on Jun. 10, 2011, now abandoned.

(51) Int. Cl.

| | |
|---|---|
| A61K 31/205 | (2006.01) |
| A61P 9/10 | (2006.01) |
| A61P 21/02 | (2006.01) |
| A61P 25/00 | (2006.01) |
| A61P 25/14 | (2006.01) |
| A61P 25/16 | (2006.01) |
| A61P 25/28 | (2006.01) |

(56) References Cited

U.S. PATENT DOCUMENTS

| | | |
|---|---|---|
| 4,343,816 A | 8/1982 | Cavazza |
| 4,346,107 A | 8/1982 | Cavazza |
| 5,192,805 A | 3/1993 | Cavazza |
| 6,572,899 B1 | 6/2003 | Gorsek |
| 2005/0043312 A1 | 2/2005 | Shea et al. |

FOREIGN PATENT DOCUMENTS

| | | |
|---|---|---|
| EP | 0514359 A2 | 11/1992 |
| EP | 0681839 A2 | 11/1995 |
| EP | 0796962 A1 | 9/1997 |
| EP | 0808626 A1 | 11/1997 |
| WO | 1998057629 A1 | 12/1998 |
| WO | 2000021526 A1 | 4/2000 |
| WO | 2000035437 A2 | 6/2000 |
| WO | 2000064426 A2 | 11/2000 |
| WO | 2001064203 A2 | 9/2001 |
| WO | 2003066041 A1 | 8/2003 |
| WO | 2003101402 A2 | 12/2003 |

OTHER PUBLICATIONS

Al-Majed, et al, "Carnitin esters prevents oxidative stress damage and energy depletion following transient forebrain ischaemia in the rat ippocampus," Clinical and Experimental Pharmacology & Physiology, vol. 33, No. 8, pp. 725-733, Aug. 2006.

Alzheimer's & Dementia Alliance of Wisconsin [online] Retrieved from the Internet, {Retrieved on Aug. 23, 2018], (Year: 2010).

Bigini et al., "Acetyl-L-carnitine shows neuroprotective and neurotrophic activity in primary culture of rat embryo motoneurons," Neuroscience Letters, vol. 329, No. 3, pp. 334-338, Sep. 2002.

De Angelis, et al., "Acetyl-L-carnitine prevents age-dependent structural alterations in rat peripheral nerves and promotes regeneration following sciatic nerve injury in young and senescent rats," Experimental Neurology, vol. 128, No. 1, pp. 103-114, Jul. 1994.

Decarolis et al., "Hippocampal neurogenesis as a target for the treatment of mental illness: a critical evaluation", Neuropharmacology. Author manuscript; available in PUbMEd Central PMC, May 1, 2011.

EMedicineHealth [online] Retrieved from the internet on Dec. 16, 2019, (Year: 2009).

Kim et al., "Treadmil exercise prevents aging-induced failure of memory through an increase in neurogenesis and suppression of apoptosis in rat hippocampus", Experimental Gerontology 45:357-365, 2010.

Kotzbauert et al., Journal of Molecular Neuroscience (2010), vol. 17, pp. 225-232 (Year: 2001).

Liu et al., "Memory loss in old rats is associated with brain mitochondrial decay and RNA_DNA oxidation: partial reversal by feeding acetyl-L-carnitine and/or R-alpha-lipoic acid", PNAS (2002), vol. 99, pp. 2356-2361.

Liu et al., PNAS (2002) vol. 99, pp. 2356-2361 (Year: 2002).

Mrak et al. (Neuropsychiatric Disease and Treatment (2007), vol. 3, pp. 619-628) (Year: 2007).

Pettegrew et al., "Acetyl-L-carnitine physical-chemical, metabolic and therapeutic properties: relevance for its mode of action in Alzheimer's disease and geriatric depression", Molecular Psychiatry, vol. 5, No. 6, pp. 616-632, Jan. 2000.

PubChem CID 7045767 [online], Retrieved from internet, [Retrieved on Aug. 23, 2018], (Year:2006).

Serajuddin Advanced Drug Delivery Reviews (2007), vol. 59, pp. 603-616 (Year::2007).

Zhang et al., J. Cell. Mol. Med (2010), vol. 14, pp. 215-225 (Year: 2010).

FIGURE 1

% MAP2-positive cells (new neurons)

ALC= acetyl L-carnitine; VPA= valproic acid.
Mean ± SD (n=3 exp, in triplicates).
Student's- test; * $p<0.05$;  $p<0.01$; * $p<0.001$; vs vehicle.

FIGURE 2

MAP2-positive cells (new neurons), nuclei are counterstained with Draq5

FIGURE 3
% of apoptosis after ALC (acetyl L-carnitine) and VPA (valproic acid) incubation ALCAR= acetyl L-carnitine.

FIGURE 4

% of necrosis after ALC (100 µM; 300 µM; and 1 mM) and VPA incubation

FIGURE 5

Specific effect of ALC on cells at various stages of differentiation

Synonymous: acetyl L-carnitine=ALC=ALCAR=L-acet.

Mean ± SD (n=3 exp, in triplicates).

Student's- test; * p<0.05;  p<0.01; * p<0.001; vs vehicle.

COMPOUNDS USEFUL FOR INCREASING NEUROGENESIS IN NEURAL TISSUE

This application is a continuation of U.S. Ser. No. 15/159,321 filed on May 19, 2016, which is a continuation of U.S. Ser. No. 13/699,930, filed on Apr. 4, 2013, now abandoned, which is a U.S. National Stage of PCT/EP2011/059665 filed on Jun. 10, 2011, which claims priority to and the benefit of European Patent Application No. 10166094.2, filed on Jun. 16, 2010, the contents of which are all incorporated herein by reference in their entireties.

FIELD OF THE INVENTION

The present invention relates to the use of alkanoyl L-carnitines for increasing neurogenesis.

In particular, the present invention relates to the use of acetyl L-carnitine or propionyl L-carnitine or a salt thereof, for increasing neurogenesis.

BACKGROUND OF THE INVENTION

Neurogenesis, or the birth of new neuronal cells, was thought to occur only in developing organisms. However, recent research has demonstrated that neurogenesis docs indeed continue into and throughout adult life in both vertebrate and invertebrate organisms. Neural stem cells (NSC) are a source for new neurons in the mammalian central nervous system (CNS). NSC are located within the ependymal and/or subventricular zone (SVZ) lining the lateral ventricle (Cell 1999; 97:703-716; Cell 1999; 96:25-34) and in the dentate gyrus of the hippocampal formation (J. Neurobiol. 1998; 36:249-266). Studies have revealed the potential for several additional locations of NSC within the adult CNS (J. Neurosci. 1999; 19:8487-8497). Asymmetric division of NSC maintains their starting number, while generating a population of rapidly dividing precursor, or progenitor cells (Cell 1999; 96:25-34). The progenitor cells respond to a range of cues that dictate the extent of their proliferation and their fate, both in terms of differentiation and positioning.

The NSC of the ventricular system in the adult are likely counterparts of the embryonic ventricular zone stem cells lining the neural tube. The progeny of these embryonic cells migrate away to form the CNS as differentiated neurons and glia (Developmental Neurobiology. 1991; pp 401-451). NSC persist in the adult lateral ventricle wall (LVW), generating neuronal progenitors that migrate down the rostral migratory stream to the olfactory bulb. There, they differentiate into granule cells and periglomerular neurons (Proc. Natl. Acad. Sci. USA 1993; 90:2074-2077). Substantial neuronal death occurs in the olfactory bulb, creating a need for continuous replacement of lost neurons which is satisfied by the migrating progenitors derived from the LVW (Neurosci. Lett. 2000; 291:17-20). In addition, there are indications that lost neurons from other brain regions can be replaced by progenitors from the LVW that differentiate into the phenotype of the lost neurons with appropriate neuronal projections and synapses with the correct target cell type (Proc. Natl. Acad. Sci. USA 1997; 94:11663-11668; Nature 2000; 405:951-955).

In vitro cultivation techniques have been established to identify the external signals involved in the regulation of NSC proliferation and differentiation (Cell 1999; 96:25-34; Exp. Cell Res. 1999; 253:733-736). The mitogens EGF and basic FGF allow cell culture expansion of neural progenitors isolated from the ventricle wall and the hippocampus (Science 1997; 276:66-71; Exp. Cell Res. 1999; 253:733-736). These dividing progenitors remain in an undifferentiated state, and grow into large clones of cells known as neurospheres. Upon the withdrawal of the mitogens and the addition of serum, the progenitors differentiate into neurons, astrocytes and oligodendrocytes, which are the three cell lineages of the brain (Cell 1999; 97:703-716; Cell 1999; 96:25-34). Specific growth factors can be added to alter the proportions of each cell type formed. For example, CNTF acts to direct the neural progenitors to an astrocytic fate (Genes Dev. 1996; 10:3129-3140; J. Neurosci. 1998; 18:3620-3629). The thyroid hormone, triiodothyronine (T3), promotes oligodendrocyte differentiation (Genes Dev. 1996; 10:3129-3140), while PDGF enhances neuronal differentiation by progenitor cells (Genes Dev. 1996; 10:3129-3140; Neuron 1997; 18:553-562). Recently, it has been shown that indeed adult regenerated neurons are integrated into the existing brain circuitry, and contribute to ameliorating neurological deficits (Cell 2002; 110:429441). Interestingly, observations have also shown that neurogenesis is occurring not only at the level of the olfactory bulb and hippocampus. In this respect it has been suggested that this process can also occur in the adult mouse substantia nigra, opening up a new field of investigation for the treatment of Parkinson s disease (Proc. Natl. Acad. Sci. USA 2003; 100:7925-7930).

The ability to expand neural progenitors and manipulate their cell fate has enormous implications for transplant therapies for neurological diseases where specific cell types are lost. Parkinson's disease (PD), for example, is characterized by degeneration of dopaminergic neurons in the substantia nigra. Previous transplantation treatments for PD patients have used fetal tissue taken from the ventral midbrain at a time when substantia nigra dopaminergic neurons are undergoing terminal differentiation (Prog. Neurobiol. 1994; 44:1-35). These cells have been grafted onto the striatum where they form synaptic contacts with host striatal neurons, their normal synaptic target. This restores dopamine turnover and release to normal levels with significant functional benefits to the patient. (Prog. Neurobiol. 1994; 44:1-35). However, the grafting of fetal tissue is limited by ethical considerations and a lack of donor tissue. The expansion and manipulation of adult NSC can potentially provide a range of well characterized cells for transplant-based strategies for neurodegenerative disease such as PD. To this aim, the identification of factors and pathways that govern the proliferation and differentiation of neural cell types is fundamentally important.

Studies have shown that intraventricular infusion of both EGF and basic FGF induces proliferation in the adult ventricle wall cell population. In the case of EGF, extensive migration of progenitors into the neighboring striatal parenchyma has been observed (J. Neurosci 1996; 16:2649-2658; J. Neurosci 1997; 17:5820-5829). EGF increases differentiation into glial lineage and reduced the generation of neurons (J. Neurosci 1997; 17:5820-5829). Additionally, intraventricular infusion of BDNF in adult rats increases the number of newly generated neurons in the olfactory bulb and rostral migratory stream, and in parenchymal structures, including the striatum, septum, thalamus and hypothalamus (J. Neurosci. 2001; 21:6706-6717). Thus, several studies have shown that the proliferation of progenitors within the SVZ of the LVW can be stimulated and that their lineage can be guided to neuronal or glial fates. Yet, the number of factors known to affect neurogenesis in vivo is small and their effects are adverse or limited.

As mentioned above, the identification of factors and pathways that govern the proliferation and differentiation of neural cell types is fundamentally important in the medical field.

The use of acetyl L-carnitine or propionyl L-carnitine in the medical field are already known.

U.S. Pat. No. 4,346,107 relates to the use of acetyl L-carnitine for the therapeutical treatment of patients with impaired cerebral metabolism, as for instance in the states of senile and presenile psychomotor involution and in senile and presenile dementia.

U.S. Pat. No. 4,343,816 relates to the use of acetyl L-carnitine for the therapeutical treatment of patients with peripheral vascular diseases such as typically, Raynaud's disease.

WO 9857629 relates to the use of acetyl L-carnitine for the therapeutical treatment of young individuals suffering from mood disorders classifiable as dysthymia (DMS IV) and a depressive, irritable, cyclothymic personality or temperament on the basis of DMS IV and AXIS II classifications, involving definite abuse of psychotropic substances.

WO 03066041 relates to the use of acetyl L-carnitine for the therapeutical treatment of depression in non demented geriatric subjects having major depressive disorder (NDG-MDD).

EP 0256999 relates to the use of acetyl L-carnitine for the therapeutical treatment of patients affected by acute or chronic peripheral neuropathy.

EP 0498144 relates to the use of acetyl L-carnitine for the therapeutical treatment of traumatic coma. In this publication is also reported that acetyl L-carnitine is able to increase the cerebral blood flow (CBF) measured by means of SPECT (Single-Photon Emission Computed Tomography).

EP 0793962 the use of propionyl L-carnitine for treating chronic arteriosclerosis obliterans in patients with severely disabling intermittent claudication.

It has been well established that new neurons are generated in the adult hippocampus throughout life by neural stem/progenitor cells (NSCs). Neurogenesis is a regenerative process responsive to external stimuli, involved in learning, memory and mood regulation. Neurogenesis is therefore believed to be an important form of neural regeneration, enabling organisms to adapt to environmental changes throughout life.

The rate of hippocampal neurogenesis significantly changes on physiological or pathological influences, such as physical activity, environmental enrichment, stress, mood disorders, ageing and neurodegenerative disorders. Indeed, during ageing, there is an age-related decline in adult neurogenesis. This decline is mostly related to decreased proliferation, associated to decreased stimulation to proliferate in an ageing brain. Natural or stimulated hippocampal neurogenesis play an important role in the clinical effects of antidepressants and possibly reduced neurogenesis may be involved in brain areas (including hippocampus) atrophy associated with depression. In Alzheimer's Disease (AD), there is also evidence for decreased neurogenesis, that accompanies the neuronal loss characteristic of the disease.

In the medical field is felt a perceived need to have available new compound, or a new use of known compound, useful for stimulating neurogenesis for the prevention of neuronal loss in normal or pathological processes in the brain.

DESCRIPTION OF THE FIGURES

In FIG. 5 is shown the specific effect of ALC on cells at various stages of differentiation. In order to better understand FIG. 5 it is important to clarify that "Nestin", an intermediate filament protein predominantly expressed by neural stem cells was used as a specific marker In fact, only nestin-positive (nestin$^+$) cells form spheres when placed in the culture conditions used for neural stem cells. In particular, mature neurons are positive for MAP2 and negative for nestin, immature neurons are positive for both MAP2 and nestin, stem progenitor cells are negative for MAP2 and positive for nestin, progenitor cells are negative for both MAP2 and nestin (see FIG. 5).

In FIG. 6 is shown that PLC and ALC are activator of NPC neuronal differentiation. In fact PLC increased the number of both mature neurons and immature neurons and reduced the number of a subpopulation of undifferentiated stem/neural progenitors, although in a lesser extent compared to ALC. On the contrary, LC had no effect.

Moreover the results demonstrated that ALC and PLC effects on NPC differentiation were not due to neuroprotective effects on newly generated immature or mature neurons.

(Synonymous: acetyl L-carnitine=ALC=ALCAR=L-acet; propionyl L-carnitine=PLC=L-Prop; LC=L-carnitine=L-car).

DESCRIPTION OF THE INVENTION

The present invention relates to an alkanoyl L-carnitine, or a salt thereof, for use for increasing neurogenesis in neural tissue.

It is therefore an object of the present invention acetyl L-carnitine or propionyl L-carnitine or a salt thereof, for use for increasing neurogenesis in neural tissue.

It is a further object of the present invention acetyl L-carnitine or propionyl L-carnitine, for use as a medicament or a food supplement for increasing neurogenesis in neural tissue; in which said increased neurogenesis is useful for preventing central nervous system disorders.

It is a further object of the present invention acetyl L-carnitine or propionyl L-carnitine, for use as a medicament or a food supplement for increasing neurogenesis in neural tissue; in which said increased neurogenesis is useful for preventing central nervous system disorders due to ageing or genetic predisposition.

It is a further object of the present invention acetyl L-carnitine or propionyl L-carnitine, for use as a medicament or a food supplement for the prevention of diseases or disturbances of the central nervous system, in which said diseases or disturbances are caused by the loss of neurons due to age or genetic predisposition.

It is a further object of the present invention acetyl L-carnitine or propionyl L-carnitine, for use as a medicament or a food supplement for the prevention of diseases or disturbances of the central nervous system, in which said diseases or disturbances respond to an increased neurogenesis.

It is a further object of the present invention the use of acetyl L-carnitine or propionyl L-carnitine, or a salt thereof, for preparing a medicament or a food supplement for increasing neurogenesis in neural tissue; in which said increased neurogenesis is useful for preventing central nervous system disorders.

It is a further object of the present invention the use of acetyl L-carnitine or propionyl L-carnitine, or a salt thereof, for preparing a medicament or a food supplement for increasing neurogenesis in neural tissue; in which said increased neurogenesis is useful for preventing central nervous system disorders due to ageing or genetic predisposition.

It is a further object of the present invention the use of acetyl L-carnitine or propionyl L-carnitine, for preparing a medicament or a food supplement for the prevention of diseases or disturbances of the central nervous system, in which said diseases or disturbances are caused by the loss of neurons due to age or genetic predisposition.

It is a further object of the present invention the use of acetyl L-carnitine or propionyl L-carnitine, for preparing a medicament or a food supplement for the prevention of diseases or disturbances of the central nervous system, in which said diseases or disturbances respond to an increased neurogenesis.

It is a further object of the present invention a method for preventing central nervous system disorders, by administering to a patient in need thereof an amount of acetyl L-carnitine or propionyl L-carnitine, suitable for increasing neurogenesis.

It is a further object of the present invention a method for preventing central nervous system disorders due to ageing or genetic predisposition, by administering to a patient in need thereof an amount of acetyl L-carnitine or propionyl L-carnitine, suitable for increasing neurogenesis.

It is a further object of the present invention a method for increasing neurogenesis, by administering to a patient in need thereof a suitable amount of acetyl L-carnitine or propionyl L-carnitine, for preventing central nervous system disorders.

It is a further object of the present invention a method for increasing neurogenesis by administering to a patient in need thereof a suitable amount of acetyl L-carnitine or propionyl L-carnitine, for preventing central nervous system disorders due to ageing or genetic predisposition.

It is a further object of the present invention a method for increasing neurogenesis, in which said increased neurogenesis is useful for preventing central nervous system disorders, by chronically administering to a patient in need thereof a suitable amount of acetyl L-carnitine or propionyl L-carnitine.

It is a further object of the present invention a method for increasing neurogenesis, in which said increased neurogenesis is useful for preventing central nervous system disorders due to ageing or genetic predisposition, by chronically administering to a patient in need thereof a suitable amount of acetyl L-carnitine or propionyl L-carnitine.

The diseases or disturbances due to genetic predisposition and/or linked to ageing, that can be prevented according to the present invention are selected from the group consisting of: neurodegenerative disorders, Parkinson's disease and Parkinsonian disorders, Huntington's disease, Alzheimer's disease, multiple sclerosis, amyotrophic lateral sclerosis, Shy-Drager syndrome, Lewy body disease, spinal ischemia, ischemic stroke, cerebral infarction, geriatric dementia, other cognitive impairments and depression.

It is evident that according to the present invention are not included patients who have traumatic disturbances of the nerves (for example injured nerves) or of the CNS (for example traumatic coma).

"Neurogenesis" is defined herein as proliferation, differentiation, migration, or survival of a neural cell in vivo or in vitro. In a preferred embodiment, the neural cell is an adult, fetal, or embryonic neural stem cell or progenitor cell. Neurogenesis also refers to a net increase in cell number or a net increase in cell survival. As used herein, "NSC" would include, at least, all brain stem cells, all brain progenitor cells, and all brain precursor cells.

In this disclosure, the terms disease or disorder shall have the same meaning.

The administration of acetyl L-carnitine or propionyl L-carnitine, may be systemic or direct into the CNS of a patient. Routes of administration include oral, subcutaneous, transdermal, intraperitoneal, intramuscular, in vein, intracerebroventricular, intraparenchymal, intrathecal, intracranial, buccal, mucosal, nasal, pulmonary, and rectal administration or administration by a liposome delivery system.

Preferably, the pharmaceutical composition is used to prevent diseases by stimulating neurogenesis (i.e., cell growth, proliferation, migration, survival and/or differentiation). For prevention, a method of the invention comprises administering to the subject an effective amount of a pharmaceutical composition including acetyl L-carnitine, or propionyl L-carnitine, in a dosage range of 0.1 g/day to 4.00 g/day; preferably in a dosage range of 1 to 2.00 g/day; most preferably 1.5 g/day in a single or multiple dose.

The composition of the invention may further comprise physiologically acceptable carriers.

According to the present invention physiologically acceptable carriers may be any carrier known in the field as suitable for pharmaceutical (i.e., topical, oral, and parenteral) application. Suitable pharmaceutical carriers and formulations are described, for example, in Remington's Pharmaceutical Sciences (19th ed.) (Genarro, ed. (1995) Mack Publishing Co., Easton, Pa.).

Any of the methods of the invention may be used to prevent a symptom of a neurological disease or disorder such as Parkinson's disease (shaking palsy), including primary Parkinson's disease, secondary parkinsonism, and postencephalitic parkinsonism; drug-induced movement disorders, including parkinsonism, acute dystonia, tardive dyskinesia, and neuroleptic malignant syndrome; Huntington's disease (Huntington's chorea; chronic progressive chorea; hereditary chorea); delirium (acute confusional state); dementia; Alzheimer's disease; non Alzheimer's dementias, including Lewy body dementia, vascular dementia, Binswanger's dementia (subcortical arteriosclerotic encephalopathy), dementia pugilistica, normal-pressure hydrocephalus, general paresis, frontotemporal dementia, multi-infarct dementia, and AIDS dementia; age-associated memory impairment (AAMI); amnesias, such as retrograde, anterograde, global, modality specific, transient, stable, and progressive amnesias, and Korsakoffs disease.

Other diseases and disorders include idiopathic orthostatic hypotension, Shy-Drager syndrome, progressive supranuclear palsy (Steele-Richardson-Olszewski syndrome); structural lesions of the cerebellum, such as those associated with infarcts, hemorrhages, or tumors; spinocerebellar degenerations such as those associated with Friedreich's ataxia, abetalipoproteinemia (e.g., Bassen-Kornzweig syndrome, vitamin E deficiency), Refsum's disease (phytanic acid storage disease), cerebellar ataxias, multiple systems atrophy (olivopontocerebellar atrophy), ataxia-telangiectasia, and mitochondrial multisystem disorders; acute disseminated encephalomyelitis (postinfectious encephalomyelitis); adrenoleukodystrophy and adrenomyeloneuropathy; Leber's hereditary optic atrophy; HTLV-associated myelopathy; and multiple sclerosis; motor neuron disorders such as amyotrophic lateral sclerosis, progressive bulbar palsy, progressive muscular atrophy, primary lateral sclerosis and progressive pseudobulbar palsy, and spinal muscular atrophies such as type I spinal muscular atrophy (Werdnig-Hoffman disease), type II (intermediate) spinal muscular atrophy, type III spinal muscular atrophy (Wohlfart-Kugelberg-Welander disease), and type IV spinal muscular atrophy.

The methods of the invention can be used to treat any mammal, including humans, cows, horses, dogs, sheep, and cats. Preferably, the methods of the invention are used to treat humans. In one aspect, the invention provides a regenerative prevention for neurological disorders by stimulating cells (e.g., stem cells) to grow, proliferate, migrate, survive, and/or differentiate to replace neural cells that have been lost or destroyed. In vivo stimulation of such cells (e.g., stem cells) can be accomplished by locally administering (via any route) the neurogenesis modulating agent of the invention to the cells in an appropriate formulation.

Pharmaceutical compositions suitable for use in the present invention include compositions wherein the active ingredients are contained in an effective amount to achieve its intended purpose. More specifically, a therapeutically effective amount means an amount effective to optimally stimulate (e.g., stem cell or progenitor cell) proliferation. It will be appreciated that the unit content of active ingredient or ingredients contained in an individual dose of each dosage form need not in itself constitute an effective amount since the necessary effective amount can be reached by administration of a plurality of dosage units (such as capsules or tablets or combinations thereof). In addition, it is understood that at some dosage levels, an effective amount may not show any measurable effect (the measurable effect could be lack of deterioration) until after a week, a month, three months, six months or a year or more of usage. Determination of the effective amounts is well within the capability of those skilled in the art. The specific dose level for any particular user will depend upon a variety of factors including the age, the physical activity level, general health, and the severity of the disorder to be prevented.

For any compound, the therapeutically effective dose can be estimated initially either in cell culture assays or in animal models, usually mice or rats.

The animal model may also be used to determine the appropriate concentration range and route of administration. Such information can then be used to determine useful doses and routes for administration in humans.

The precise effective dose for a human subject will depend upon the severity of the disease state, general health of the subject, age, weight, and gender of the subject, diet, time and frequency of administration, reaction sensitivities, and tolerance/response to therapy. This amount can be determined by routine experimentation and is within the judgement of the clinician.

What is meant by salt of acetyl L-carnitine or propionyl L-carnitine, is any salt with an acid that does not give rise to toxic or side effects.

Non-limiting examples of such salts are: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

A list of FDA-approved pharmaceutically acceptable salts is given in the publication Int. J. of Pharm. 33 (1986), 201-217.

Acetyl L-carnitine or propionyl L-carnitine are known compounds and their preparation process is described in U.S. Pat. No. 4,254,053. Their procurements therefore is very easy, inasmuch as these products have been on the market now for a long time and are of a grade suitable for human administration.

As shown in the experimental part reported in the following, the neurogenic activity of acetyl L-carnitine or propionyl L-carnitine according to the present invention is not correlated to their neuroprotective activity.

In fact, at the concentrations that induced neurogenesis acetyl L-carnitine and propionyl L-carnitine did not reduce the percentage of apoptotic nuclei or the activity of the LDH enzyme, an index of necrosis.

The following non limiting examples further illustrate the invention.

Example 1

In Vitro ALC Modulates Neuronal Differentiation of Adult Neural Progenitors Taken from the Mouse Hippocampus Introduction Complex set of events related to cell proliferation, differentiation, migration and survival that characterize adult neurogenesis starting from neural stem cells takes place even during adulthood. These events take place principally in two separate regions of the brain: the subgranular zone in the fascia dentata hippocampi (SubGranular Zone, SGZ) and the subventricular zone in the wall of the lateral ventricle (SubVentricular Zone, SVZ), where there is believed to be a favourable microenvironment (niche) that enables the stem cell to survive and divide periodically and asymmetrically giving rise to rapidly dividing progenitors some of which move towards neuronal differentiation.

MATERIALS AND METHODS

Animals and Preparation of Hippocampal Neurospheres in Culture

The adult stem cells from the mouse hippocampus were prepared and maintained in culture in the form of neurospheres as described previously in Denis-Donini S. et al. J. Neuroscience, 2008. In particular, male CD1 mice aged 3-5 months were used, in accordance with the animal experimentation laws.

Proliferation of Stem Cells/Adult Neural Progenitors

Neurospheres with passages of between 4-12 were dissociated and plated at a density of $1 \times 10^5$ cells/ml in a 96-well plate in ALC (0.1-2 mM) at different concentrations or a vehicle. After 24, 48, 72 and 96 hours, the cells were processed to measure the amount of cell ATP present using the CellTiter-Glow™ Luminescent kit (Promega).

Differentiation of Stem Cells/Adult Neural Progenitors

For differentiation, the cells derived from the hippocampal neurospheres with passages of between 4-12 were dissociated and plated on Lab-Tek 8-well permanox chamber slides (Nunc, Wiesbaden, Germany) previously coated with mouse laminin (2.5 µg/cm$^2$ Sigma) at a density of about 40,000 cells/cm$^2$. The composition of the differentiation medium was: Neurobasal-A, supplement B27, glutamine 2 mM, 100 U/100 µg/ml penicillin/streptomycin. ALC (0.1-2 mM) or a vehicle was added to the medium. After 24 hours the cells were washed and fixed in 4% paraformaldehyde for 20 min for subsequent analysis using immunofluorescence.

Analysis Using Immunofluorescence

The cells fixed after differentiation in the presence of ALC, a vehicle or reference drugs were washed three times in PBS and permeabilized by incubation for 5 min, at room temperature with PBS supplemented with 0.48% (vol/vol) Triton X-100 (Sigma). Subsequently the cells were incubated with the following primary antibodies: anti-nestin mouse monoclonal antibody, 1:1200, Abcam, Cambridge, Mass.); anti-MAP-2 (rabbit polyclonal antibody, 1:600, Chemicon). The cells were incubated in the primary antibody for 150 min at room temperature in a solution containing 8% (vol/vol) of goat serum. The secondary antibodies used were: Alexa Fluor 594-conjugated donkey anti mouse antibody (1:1400, Molecular Probes), Alexa Fluor 488-conjugated donkey anti-rabbit (1:1 600, Molecular Probes), in a solution containing 16% (vol/vol) of donkey serum. The nuclei were then counterstained with Draq5 (1:2000, Alexis Biochemicals) prepared in PBS. The slides were assembled using Fluorescent Mounting Medium (DakoCytomation, Glostrup).

In each experiment, the cells of at least 5 fields/well (corresponding to about 150 cells), were quantified if positive to one or more phenotypical markers used to distinguish between them: undifferentiated stem progenitor cells, immature neurons, mature neurons. The cells were counted by an operator (blind to the nature of the treatment undergone by the cells) using an ECLIPSE E600 fluorescence microscope (NIKON, Calenzano, Italy) with a 60× lens. All experiments were conducted on at least five cell preparations, with each experimental point in triplicate.

Assessment and Cell Survival

After differentiation in the presence of ALC, a vehicle or reference drugs, the medium was collected and the activity of the LDH enzyme was determined using the Cytotoxicity Detection Kit LDH (Roche Applied Science), following the manufacturer's instructions, to quantify death due to necrosis. In parallel, to assess also apoptotic death, after fixation, the cell nuclei were marked with 0.8 ng/ml Hoechst (Sigma-Aldrich) diluted in PBS. The apoptic nuclei were counted by an operator (blind to the nature of the treatment undergone by the cells) using an ECLIPSE E600 fluorescence microscope (NIKON, Calenzano, Italy) with a 60× lens. All experiments were conducted on at least five cell preparations, with each experimental point in triplicate.

Results

In this study the microtubule associated protein 2 (MAP2) was used as a neuron-specific marker. MAP-2 is the major microtubule-associated protein of brain tissue. There is some indication that MAP2 is expressed at higher levels in some types of neurons than in others. MAP2 is known to promote microtubule assembly and to form side-arms on microtubules, which is an essential step in neurogenesis. It also interacts with neurofilaments, actin, and other elements of the cytoskeleton.

Figure 1:
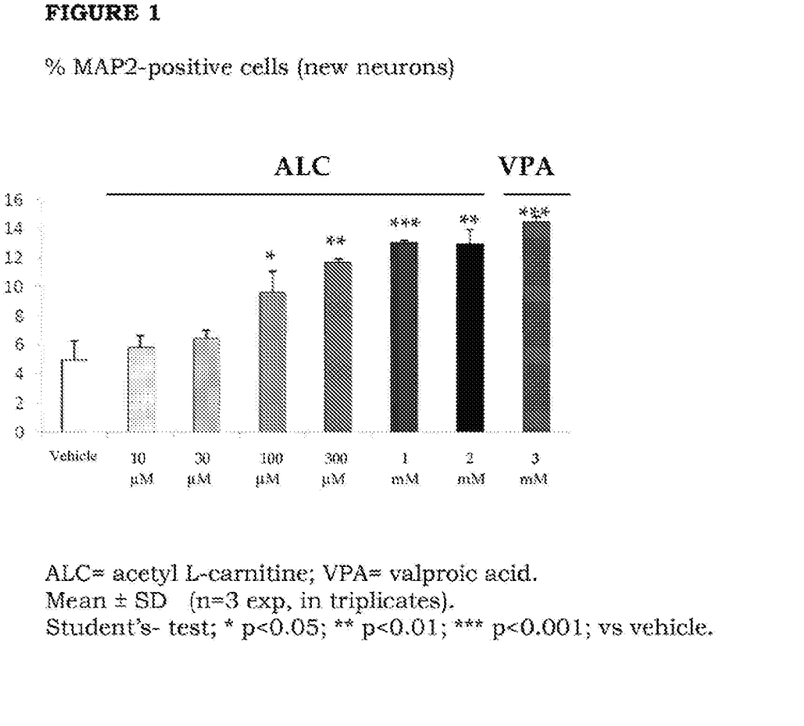
FIG. 1 describes that ALC has a concentration-dependent strengthening effect on the differentiation of stem cells/adult progenitors to mature and immature neurons. In fact, ALC has a marked concentration-dependent hippocampal neurogenic activity as demonstrated by the increase in the percentage of MAP-2 positive cells (i.e. new neurons) in culture.

In adult neurospheres from the mouse hippocampus compared to valproic acid (VPA), a positive neurogenesis modulator, it has been demonstrated that ALC has a dose-dependent strengthening effect on the differentiation of stem cells/adult progenitors to mature and immature neurons (FIG. 1). In fact, ALC has a marked concentration-dependent hippocampal neurogenic activity as demonstrated by the increase in the percentage of MAP-2 positive cells in culture.

Figure 2:
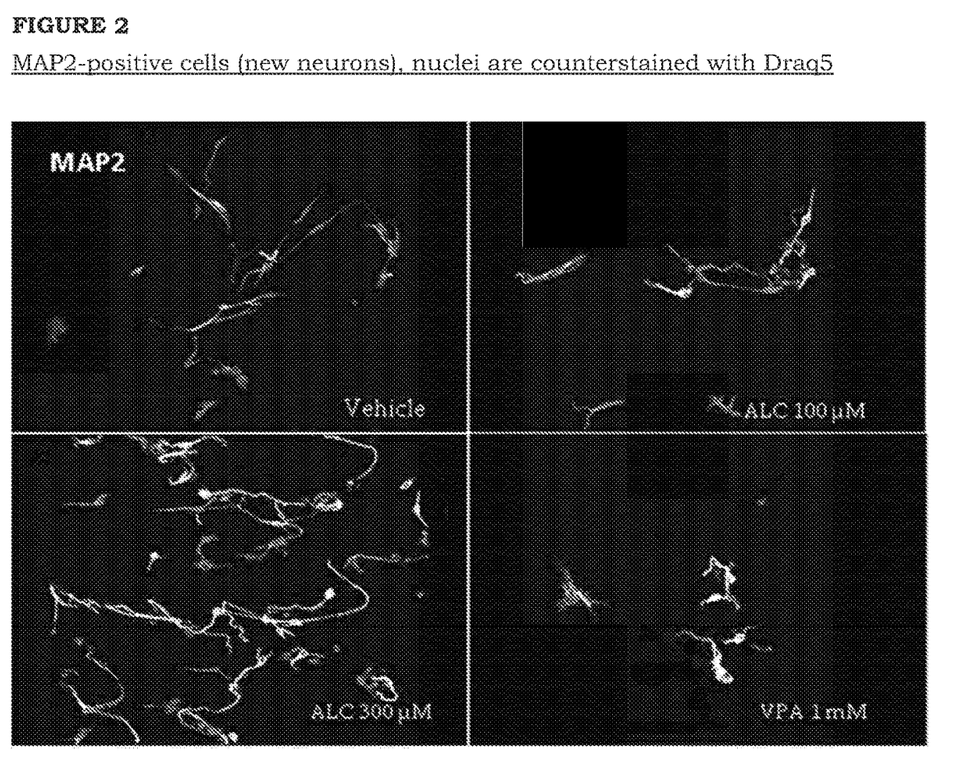
FIG. 2 shows the hippocampal neurogenic activity of ALC (MAP2-positive cells evaluated by MAP-2 staining in cultured neurons by immunofluorescence staining. Nuclei were stained with Draq5.

The hippocampal neurogenic activity of ALC was also evaluated by MAP-2 staining (green) in cultured neurons by immunofluorescence staining. Nuclei were stained with Draq5 (FIG. 2).

Figure 3:
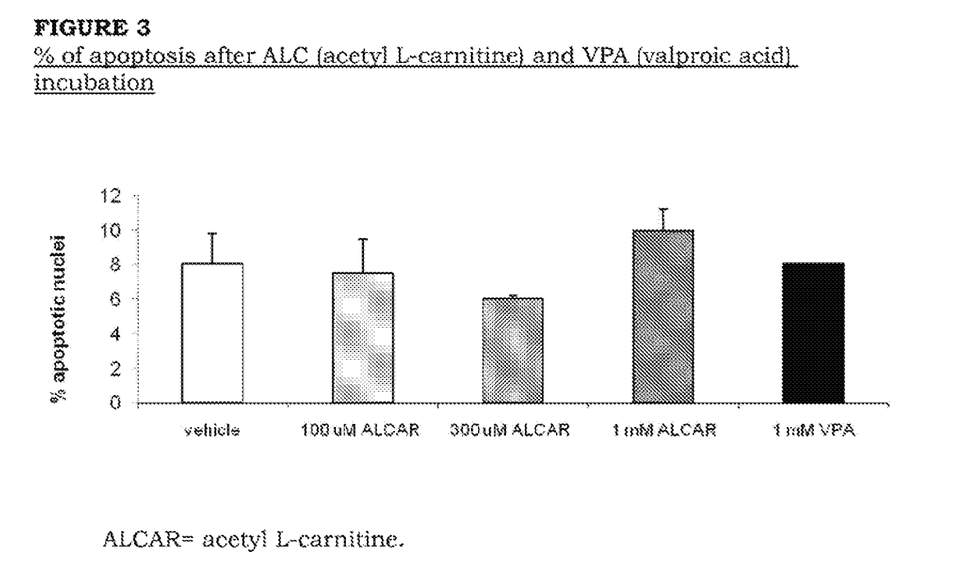
FIGS. 3 and 4 describe that the neurogenic activity of ALC is not correlated to neuroprotective activity. In fact, at the concentrations that induced neurogenesis, ALC (100 µM; 300 µM or 1 mM) did not reduce the percentage of apoptotic nuclei (FIG. 3) or even the activity of the LDH enzyme, an index of necrosis (FIG. 4).
Figure 4:
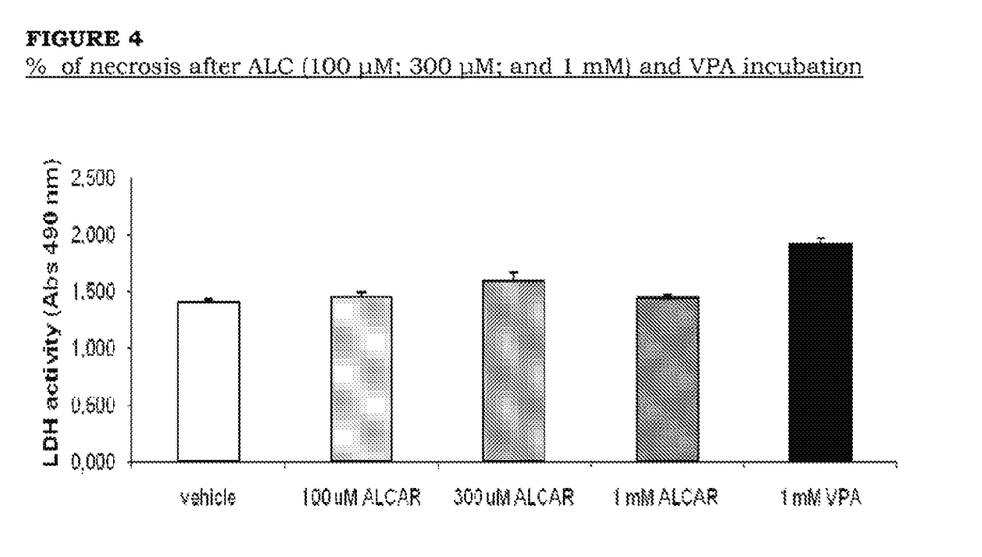

The neurogenic activity of ALC is not correlated to neuroprotective activity. In fact, at the concentrations that induced neurogenesis, ALC (100 µM; 300 µM or 1 mM) did not reduce the percentage of apoptotic nuclei (FIG. 3) or even reduce the activity of the LDH enzyme, an index of necrosis, in the culture medium (FIG. 4).

Figure 5:
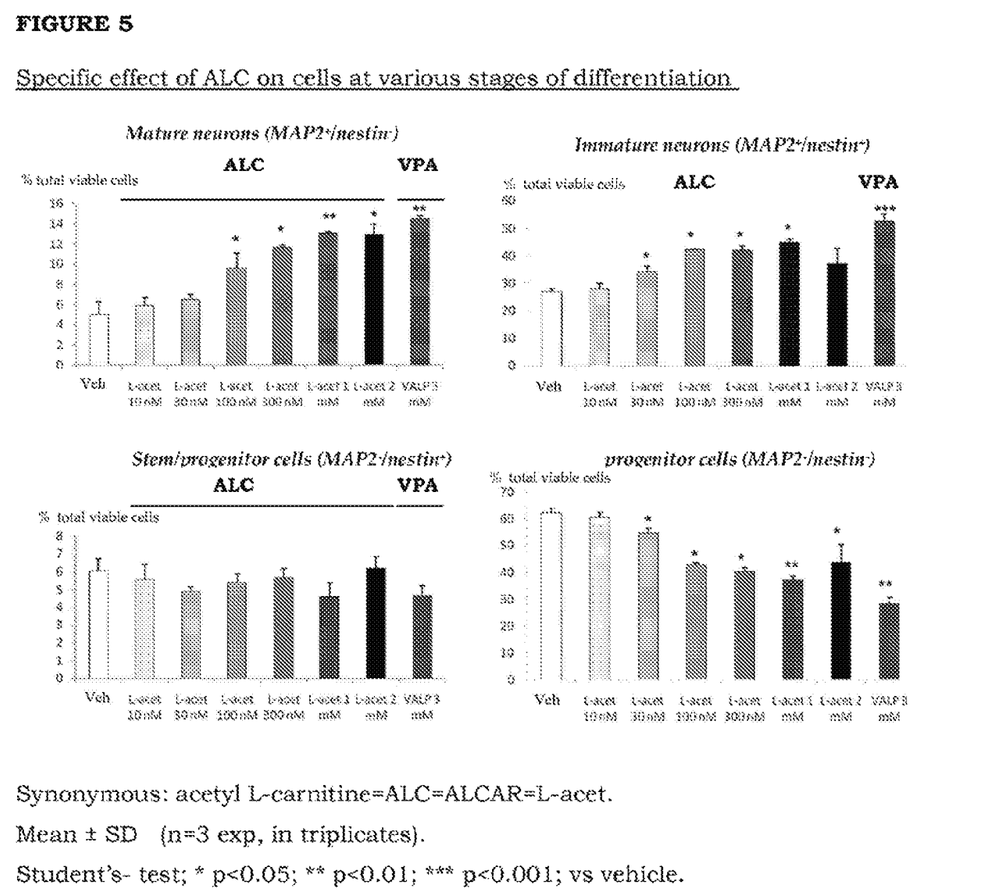

Nestin, an intermediate filament protein predominantly expressed by neural stem cells was also used as a specific marker. In fact, only nestin-positive cells form spheres when placed in the culture conditions used for neural stem cells. In particular, mature neurons are positive for MAP2 and negative for nestin, immature neurons are positive for both MAP2 and nestin, stem/progenitor cells are negative for MAP2 and positive for nestin, and progenitor cells are negative for both MAP2 and nestin (FIG. 5).

Treatment with ALC increased the number of mature neurons in a concentration-dependent manner, as well as the number of immature neurons; ALC had no effect on the number of stem/progenitor cells and decreased the number of progenitor cells.

The experimental data reported in FIGS. 1-6 show that ALC and PLC are able to promote the neuronal differentiation of adult mouse hippocampal neural progenitors. In particular, ALC increases the number of both mature neurons and immature neurons; reduces the number of a subpopulation of undifferentiated stem/neural progenitors; and carries out an activity that is not due to its neuroprotective effect.

Example 2

Figure 6:
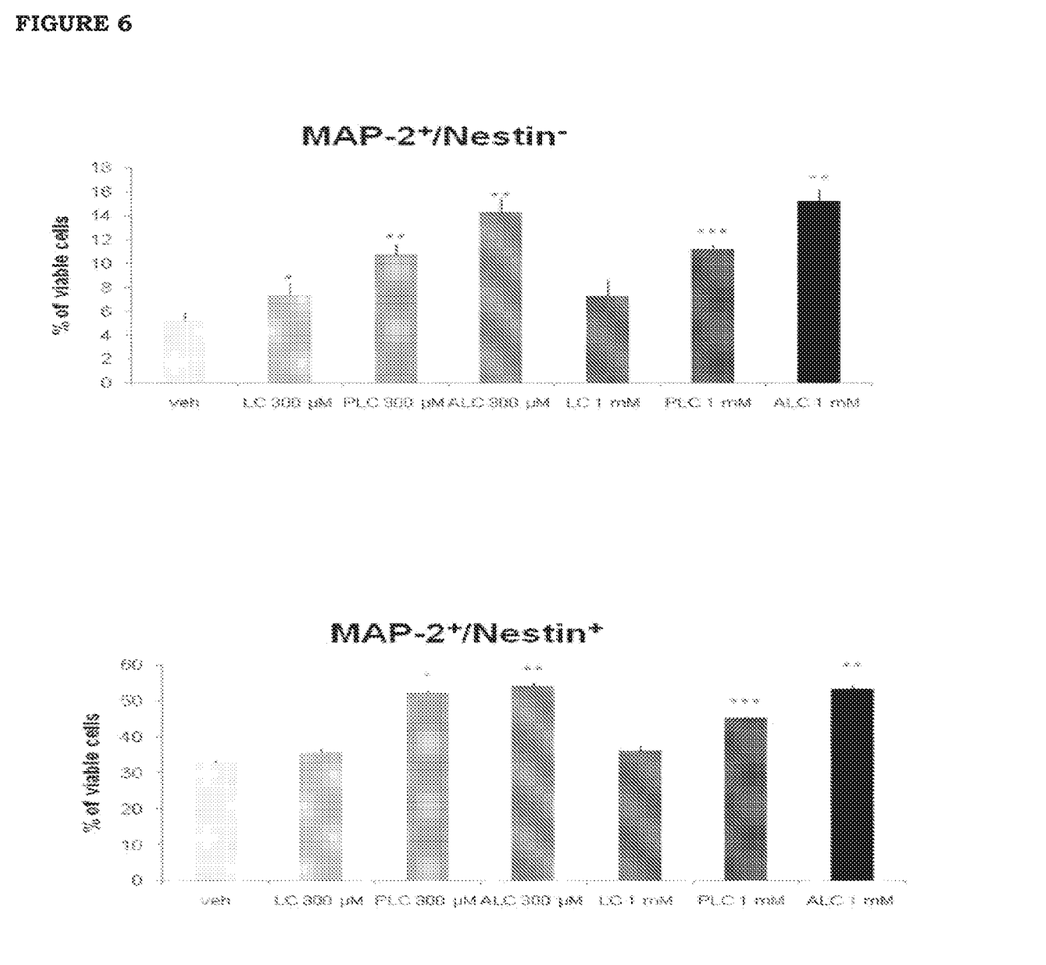

In Vitro Comparison of ALC PLC and LC on Modulation of Neuronal Differentiation of Adult Neural Progenitors Taken from the Mouse Hippocampus In example 2, by using the same experimental procedures as for example 1, the activity of ALC (1 mM) as a modulator of adult hippocampal neurogenesis in an in vitro model of adult neural progenitor cells has been compared to that of propionyl-L-carnitine (PLC) (0.3-1 mM) and L-carnitine (LC) (0.3-1 mM). As reported in FIG. 6, compared to ALC, PLC appeared to be a less potent activator of NPC neuronal differentiation. In fact PLC increased the number of both mature neurons and immature neurons and reduced the number of a subpopulation of undifferentiated stem/neural progenitors, although in a lesser extent compared to ALC. On the contrary, LC had no effect. Moreover the results demonstrated that ALC and PLC effects on NPC differentiation were not due to neuroprotective effects on newly generated immature or mature neurons.

The invention claimed is:

1. A method for increasing neurogenesis in a patient in need thereof, said method consisting of administering to said patient in need a dose of an active agent, said active agent consisting of acetyl L-carnitine or a salt thereof, wherein said dose corresponds to 1.00 g/day to 2.00 g/day administered in a single or multiple doses, and
    increasing said neurogenesis in said patient.

2. The method of claim 1, wherein the salt of acetyl L-carnitine is selected from the group consisting of: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

3. The method of claim 1, wherein the acetyl L-carnitine is administered in a dose of 1.5 g/day, in a single or multiple doses.

4. The method of claim 1, wherein the acetyl L-carnitine is administered by oral, subcutaneous, transdermal, intraperitoneal, intramuscular, in vein, intracerebroventricular, intraparenchymal, intrathecal, intracranial, buccal, mucosal, nasal, pulmonary, rectal administration or by a liposome delivery system.

* * * * *